United States Patent
Minote et al.

(10) Patent No.: US 10,161,892 B2
(45) Date of Patent: Dec. 25, 2018

(54) METHOD OF ANALYZING PRESS FORMING

(71) Applicant: JFE STEEL CORPORATION, Tokyo (JP)

(72) Inventors: Toru Minote, Tokyo (JP); Yuichi Tokita, Tokyo (JP); Yoshikiyo Tamai, Tokyo (JP); Takeshi Fujita, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 726 days.

(21) Appl. No.: 14/766,682

(22) PCT Filed: Feb. 8, 2013

(86) PCT No.: PCT/JP2013/000704
§ 371 (c)(1),
(2) Date: Aug. 7, 2015

(87) PCT Pub. No.: WO2014/122695
PCT Pub. Date: Aug. 14, 2014

(65) Prior Publication Data
US 2015/0377806 A1 Dec. 31, 2015

(51) Int. Cl.
*G01L 1/00* (2006.01)
*B21D 22/02* (2006.01)
(Continued)

(52) U.S. Cl.
CPC .......... *G01N 25/00* (2013.01); *B21D 22/022* (2013.01); *B21D 22/208* (2013.01); *G01B 21/20* (2013.01);
(Continued)

(58) Field of Classification Search
CPC ....... C22C 38/06; C22C 38/32; C22C 38/002; C22C 38/02; C22C 38/04; C22C 38/18;
(Continued)

(56) References Cited

U.S. PATENT DOCUMENTS

| | | |
|---|---|---|
| 2004/0176863 A1 | 9/2004 | Ren et al. |
| 2010/0005845 A1 | 1/2010 | Yoshida et al. |

(Continued)

FOREIGN PATENT DOCUMENTS

| | | |
|---|---|---|
| CN | 1178143 A | 4/1998 |
| CN | 101169642 A | 4/2008 |

(Continued)

OTHER PUBLICATIONS

Berry et al., Stamping Out Forming Problems with FEA, Mechanical Engineering; Jul. 1988; 110, 7; ProQuest p. 58.*

(Continued)

*Primary Examiner* — Roy Y Yi
(74) *Attorney, Agent, or Firm* — Oliff PLC

(57) ABSTRACT

A method of analyzing press-forming of a press-forming material including analyzing press-forming, analyzing springback and analyzing a change in shape of the press-forming material. The analyzing press-forming may include setting an initial temperature distribution for the heated press-forming material and performing a press-forming analysis by combining temperature analysis and structural analysis to obtain shape information, temperature distribution, stress distribution, and strain distribution. The analyzing springback may occur with and without consideration of contact heat transfer between a press-forming tool and the press-forming material. The method may further include modifying the temperature distribution obtained in the analyzing springback and then re-analyzing the change in shape of the press-forming material. The analyzing the change in shape may be performed until a temperature distribution in the press-forming material is within the range of ±5° C.

6 Claims, 6 Drawing Sheets

(51) Int. Cl.
   *G01N 25/00*   (2006.01)
   *B21D 22/20*   (2006.01)
   *G01B 21/20*   (2006.01)
   *G06F 17/50*   (2006.01)
(52) U.S. Cl.
   CPC ............ *G01L 1/00* (2013.01); *G06F 17/5009* (2013.01); *G06F 17/5086* (2013.01); *G06F 2217/80* (2013.01)
(58) Field of Classification Search
   CPC ......... C22C 38/26; C22C 45/02; C22C 21/02; C22C 38/005; C22C 38/008; C22C 38/28; C22C 38/38; C22C 1/026; C22C 2200/02
   See application file for complete search history.

(56) References Cited

U.S. PATENT DOCUMENTS

| | | | |
|---|---|---|---|
| 2010/0018277 | A1 | 1/2010 | Hielscher |
| 2015/0039247 | A1* | 2/2015 | Minote ................ B21D 22/208 702/42 |

FOREIGN PATENT DOCUMENTS

| | | |
|---|---|---|
| CN | 101522332 A | 9/2009 |
| EP | 2058062 A1 | 5/2009 |
| EP | 2371464 A1 | 10/2011 |
| JP | H07-155853 A | 6/1995 |
| JP | 2001-314923 A | 11/2001 |
| JP | 2004-270006 A | 9/2004 |
| JP | 2007-229724 A | 9/2007 |
| JP | 2008-055476 A | 3/2008 |
| JP | 2008-273796 A | 11/2008 |
| JP | 2010-207910 A | 9/2010 |
| JP | 2011-107759 A | 6/2011 |
| JP | 2011-161481 A | 8/2011 |
| KR | 2009-0046906 A | 5/2009 |

OTHER PUBLICATIONS

Ozturk et al. Journal of Iron and Steel Research, International Tensile and Spring-Back Behavior of DP600 Advance High Strength Steel at Warm Temperature, 2009.*
Li et al. Coupled Numerical Simulation of Hot Stamping Process and Experimental Verification, America Institute of Physics, AIP Conference Proceedings 1532, 471, 2013.*
Laurent et al., Mechanical Behaviour and Springback Study of an Aluminium Alloy in Warm Forming Conditions, ISRN Mechanical Engineering, vol. 2011, Article ID 381615 (Year: 2011).*
Gisario et al., Springback control in sheet metal bending by laser-assisted bending: Experimental analysis, empirical and neural network modelling, Optics and Lasers in Engineering 49 (2011), 1372-1383 (Year: 2011).*
May 14, 2013 International Search Report issued in International Application No. PCT/JP2013/000704.
Jun. 9, 2015 Office Action issued in Japanese Patent Application No. 2011-201312.
Jun. 30, 2015 Office Action issued in Japanese Patent Application No. 2011-201315.
Katsuhisa Osawa, "Coupled Numerical Simulation of Heat Transfer and Sheet Metal Forming in Die Quenching Method", Proceedings of the 54th Japanese Joint Conference for the Technology of Plasticity, pp. 449-450 (Nov. 2003).
Myoung-Gyu Lee et al., "Finite element investigations for the role of transformation plasticity on springback in hot press forming process" Computational Materials Science; No. 47; 2009; pp. 556-567.
May 11, 2016 Search Report issued in European Patent Application No. 13874279.6.
Jul. 4, 2016 Office Action issued in Chinese Patent Application No. 201380072444.X.
Jul. 4, 2016 Office Action issued in Korean Patent Application No. 2015-7021668.

* cited by examiner

DISTANCE MEASURED FROM ONE END PORTION ALONG CROSS-SECTIONAL SURFACE

LENGTH MEASURED FROM CENTER IN WIDTH DIRECTION ALONG CROSS-SECTIONAL SURFACE

METHOD OF ANALYZING PRESS FORMING

TECHNICAL FIELD

This application is directed to a method of analyzing press forming, and particularly to a method of analyzing press forming that estimates a shape of a press-forming material that is cooled after being heated for press forming.

BACKGROUND

Press forming is a process of transferring a shape of a tool to a target press-forming material (metal sheet) by pressing the tool to the press-forming material. In press forming, after a press-formed material removed from the tool (after release from a tool) springback (elastic deformation) arises and the press-formed material has often an undesirable shape.

Such springback is known to be caused by residual stress in a press-formed material before release from the tool. Conventionally, a numerical analysis method such as a finite element method has been used to estimate the shape after springback and to analyze the cause of the springback.

A conventional analysis of factors contributing to the springback includes a "press-forming analysis method" disclosed in Patent Literature 1. The "press-forming analysis method" disclosed in Patent Literature 1 includes the following three processes.

Process 1 includes calculating data of, for example, a shape of a press-formed material before release from a tool. By the process 1, it is performed, based on the data before release from the tool, to calculate data of a shape of the press-formed material after release from the tool and to calculate a defined quantity relating to springback.

Process 2 includes adding a modification to a distribution of residual stress in a specific region of the press-formed material before release from the tool. By the process 2, it is performed, based on the modified data, to calculate data of, for example, a shape of the press-formed material after release from the tool, and to calculate a defined quantity relating to the springback after the modification in the distribution of the residual stress in the specific region.

Process 3 includes calculating how the defined quantity is changed by the modification to the distribution of the residual stress in the specific region.

The "press-forming analysis method" in Patent Literature 1 quickly and accurately estimates an effect of residual stress on springback in any region of a press-formed material after press forming (before release from a tool) for consideration of countermeasures for springback.

In conventional methods of analyzing springback, as represented by Patent Literature 1, the press forming discussed therein is cold press forming in which a press-forming material is not heated.

In recent years, a high strength steel sheet has been more widely used as a steel sheet for automotive parts to improve both fuel efficiency and collision safety performance.

Since the high strength steel sheet has high flow stress to deformation, service life of the tool is shortened if the high strength steel sheet is processed by cold press forming. The high strength steel sheet can be processed by only limited processes such as deep-drawing and high stretch-flanging, which are not high-pressure processes.

To avoid such problems, "warm press forming" that performs press forming after a press-forming material is heated to a predetermined temperature is used for the high strength steel sheet. Warm press forming is performed at a higher temperature than in cold press forming, and decrease the flow stress of the high strength steel sheet to improve deformability. This technique prevents defects such as cracks from occurring in press forming. Such a technique of the warm press forming is disclosed in Patent Literature 2, for example.

CITATION LIST

Patent Literature

PTL 1: Japanese Unexamined Patent Application Publication No. 2007-229724
PTL 2: Japanese Unexamined Patent Application Publication No. 2001-314923

SUMMARY

Technical Problem

A springback analysis was performed after release from a tool by using a finite element method to study a shape defect in high strength steel after warm press forming. A comparison was made between the shape obtained by the springback analysis and the shape of the press-formed material obtained by the actual warm press forming. As a result of the comparison, a big difference was found.

It was found from the above that a final shape or the cause is impossible to be analyzed unless thermal contraction during cooling is taken into account, because the temperature of the press-formed material obtained by the warm press forming is high immediately after the release from the tool.

However, the conventional technique performs the press-forming analysis and the springback analysis for consideration of countermeasures for the shape defect under assumption of the cold press forming, and the technique does not consider a temperature distribution generated in the press-forming material. Thus, the conventional technique cannot perform an analysis for consideration of countermeasures for a shape defect, which may occur in the warm press forming.

Disclosed embodiments were made to solve the above-described problems. It is an object of this disclosure to provide a method of analyzing press forming that estimates a shape after cooling in warm press forming.

Solution to Problem

The method of analyzing press forming in the present description includes a press-forming analysis that analyzes a state of a formed press-forming material before release from a tool, a springback analysis that analyzes springback of the press-forming material after release from the tool, and a shape analysis that analyzes a change in shape of the press-forming material after springback due to a change in temperature. It was found that the shape defect arising in the warm press forming is affected not only by residual stress at a bottom dead point but also by a temperature distribution, and also found that thermal contraction during cooling based on the temperature distribution should be taken into consideration, because the temperature of the press-formed material obtained by the warm press forming is high immediately after the release from the tool. Based on the findings, further study was conducted and it was found that the above-described problems can be solved by the steps of performing press forming to a heated press-forming material, obtaining a temperature distribution at the time of springback, and analyzing a change in shape caused by thermal contraction during cooling based on the temperature distribution.

Disclosed embodiments are based on the above and specific configurations of the embodiments are as follows.

(1) A method of analyzing press forming including:

performing a step of analyzing press forming including setting an initial temperature distribution for a heated press-forming material and performing a press-forming analysis by combining a temperature analysis and a structural analysis to obtain shape information, temperature distribution, stress distribution, and strain distribution after press forming and before release from a tool;

performing a step of analyzing springback including performing a springback analysis by combining a temperature analysis and a structural analysis without consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback; and performing a step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback.

(2) A method of analyzing press forming including:

performing a step of analyzing press forming including setting an initial temperature distribution for a heated press-forming material and performing a press-forming analysis by combining a temperature analysis and a structural analysis to obtain shape information, temperature distribution, stress distribution, and strain distribution after press forming and before release from a tool;

performing a step of analyzing springback including performing a springback analysis by combining a temperature analysis and a structural analysis in consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback; and performing a step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback.

(3) The method of analyzing press forming according to (1) or (2), wherein the structural analysis in the step of analyzing a shape includes a final step that is performed by a static implicit method.

(4) A method of analyzing press forming including:

performing a step of analyzing press forming including setting an initial temperature distribution for a heated press-forming material and performing a press-forming analysis by combining a temperature analysis and a structural analysis to obtain shape information, temperature distribution, stress distribution, and strain distribution in the press-forming material before release from a tool;

performing a step of analyzing springback including performing a springback analysis by combining a temperature analysis and a structural analysis without consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback;

performing a first step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback;

performing a second step of analyzing a shape including
adding a modification to the temperature distribution obtained in the step of analyzing springback and performing an analysis of a change in shape of the press-forming material that occurs during and after cooling, until a range of the temperature distribution in the press-forming material falls within ±5° C., by combining a temperature analysis and a structural analysis based on the modified temperature distribution, the shape information, the stress distribution, and the strain distribution obtained in the step of analyzing springback; and performing a step of comparing shapes including comparing shapes of the press-forming materials after cooling obtained by the analysis in the second step of analyzing a shape and the analysis in the first step of analyzing a shape.

(5) A method of analyzing press forming including:

performing a step of analyzing press forming including setting an initial temperature distribution for a heated press-forming material and performing a press-forming analysis by combining a temperature analysis and a structural analysis to obtain shape information, temperature distribution, stress distribution, and strain distribution in the press-forming material before release from a tool;

performing a step of analyzing springback including performing a springback analysis by combining a temperature analysis and a structural analysis in consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback;

performing a first step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback;

performing a second step of analyzing a shape including adding a modification to the temperature distribution obtained in the step of analyzing springback and performing an analysis of a change in shape of the press-forming material that occurs during and after cooling, until a range of the temperature distribution in the press-forming material falls within ±5° C., by combining a temperature analysis and a structural analysis based on the modified temperature distribution, the shape information, the stress distribution, and the strain distribution obtained in the step of analyzing springback; and performing a step of comparing shapes including comparing shapes of the press-forming materials after cooling obtained by the analysis in the second step of analyzing a shape and the analysis in the first step of analyzing a shape.

(6) The method of analyzing press forming according to (4) or (5), wherein the structural analysis in each of the first step of analyzing a shape and the second step of analyzing a shape includes a final step that is performed by a static implicit method.

Advantageous Effects

According to disclosed embodiments, a shape after cooling in the warm press forming can be estimated. Thus, countermeasures for a shape defect in the warm press forming can be taken, and advantages such as reduction in the number of test steps in a design stage of a press-formed material and reduction in the cost may be obtained.

DETAILED DESCRIPTION

First Embodiment

A method of analyzing press forming in a first embodiment is performed by an apparatus such as a PC (personal computer) that runs programs. First, a configuration of an apparatus (hereinafter, referred to as "apparatus for analyzing press forming 1") is briefly described with reference to a block diagram in FIG. 2.

Apparatus for Analyzing Press Forming

Figure 2:
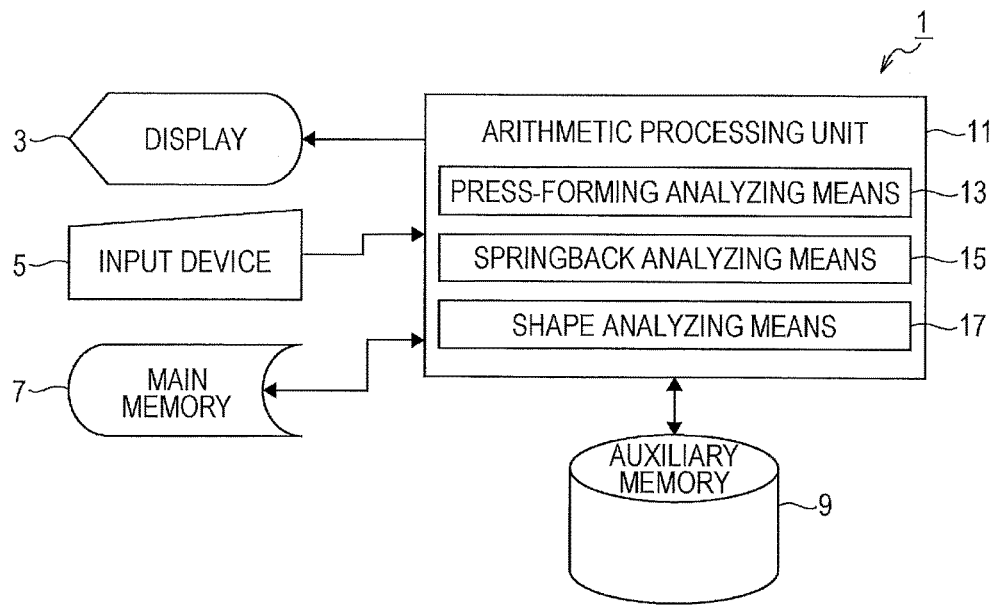
FIG. 2 is a block diagram illustrating a configuration of an apparatus according to an embodiment.

An apparatus for analyzing press forming 1 in the first embodiment is a PC (personal computer), for example, and includes a display 3, an input device 5, a main memory 7, an auxiliary memory 9, and an arithmetic processing unit 11, as illustrated in FIG. 2.

The display 3, the input device 5, the main memory 7, and the auxiliary memory 9 are coupled to the arithmetic processing unit 11 and each operate in response to a command from the arithmetic processing unit 11. The display 3 displays a calculation result and the like, and is an LCD monitor and the like.

The input device 5 is used by an operator for input and the like, and is a keyboard or a mouse and the like.

The main memory 7 temporarily stores data to be used in the arithmetic processing unit 11 or data being processed, for example, and is a RAM and the like. The auxiliary memory 9 stores data and the like, and is a hard disk and the like.

The arithmetic processing unit 11 is a CPU and the like, of a PC and the like. The arithmetic processing unit 11 includes a press-forming analyzer 13, a springback analyzer 15, and a shape analyzer 17. The analyzers operate when the CPU and the like, runs a predetermined program. Hereinafter, the analyzers are described.

<Press-Forming Analyzing Means>

The press-forming analyzing means 13 is configured to set an initial temperature distribution for a heated press-forming material and perform a press-forming analysis by combining a temperature analysis and a structural analysis to obtain shape information, temperature distribution, stress distribution, and strain distribution after press forming (before release from a tool).

<Springback Analyzing Means>

The springback analyzing means 15 is configured to perform a springback analysis by combining a temperature analysis and a structural analysis to obtain shape information, temperature distribution, stress distribution, and strain distribution after springback based on the information obtained by the press-forming analyzing means 13.

<Shape Analyzing Means>

The shape analyzing means 17 is configured to analyze a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained by the springback analyzing means 15.

Method of Analyzing Press Forming

A method of analyzing press forming in the first embodiment is performed when each of the above-described "press-forming analyzing means", "springback analyzing means", and "shape analyzing means" performs its function and includes the following steps.

Specifically, the method of analyzing press forming in the first embodiment includes performing a step of analyzing press forming including setting an initial temperature distribution for a heated press-forming material and performing a press-forming analysis by combining a temperature analysis and a structural analysis to obtain shape information, temperature distribution, stress distribution, and strain distribution after press forming (before release from a tool), performing a step of analyzing springback including performing a springback analysis by combining a temperature analysis and a structural analysis without consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback, and performing a step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback.

In the method of analyzing press forming in the first embodiment, the analysis is performed by combining the temperature analysis and the structural analysis in each step as described above. In the analysis performed by combining the temperature analysis and the structural analysis, the temperature distribution in the press-forming material is analyzed (temperature analysis) in consideration of air cooling and contact heat transfer between the tool and the press-forming material, for example, and a pressed condition and the like, is analyzed (structural analysis) by using temperature dependency data (Young's modulus, Poisson's ratio, thermal expansion coefficient, yield stress, a stress-strain curve, specific heat, and thermal conductivity, for example) corresponding to the temperature based on the obtained temperature distribution.

Figure 1:
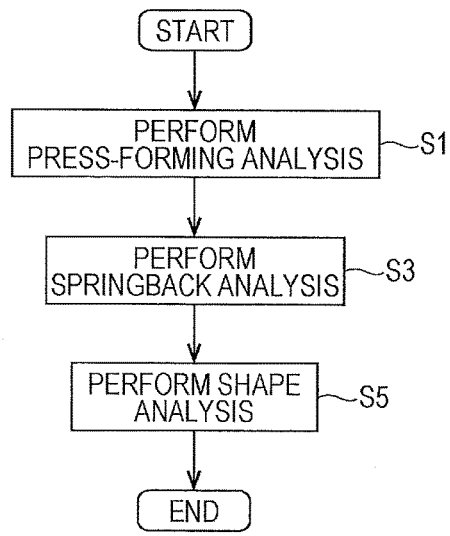
FIG. 1 is a flowchart of processing according to an embodiment.

Hereinafter, each of the above-described steps in the method of analyzing press forming in the first embodiment is described in detail with reference to the flowchart in FIG. 1.

<Step of Analyzing Press Forming>

The step of analyzing press forming includes setting an initial temperature distribution for a heated press-forming material, and performing a press-forming analysis by combining a temperature analysis and a structural analysis to obtain shape information, temperature distribution, and stress distribution, and strain distribution after press forming (before release from a tool) (Step S1).

Setting the initial temperature distribution for the heated press-forming material is described below.

In actual warm press forming, a press-forming material is sufficiently heated in an electric furnace to have a uniform temperature and is then transferred to a pressing machine by a transfer robot for press forming. In the step of analyzing press forming, the initial temperature of the entire press-forming material is set to be uniform (600° C., for example) assuming that the press-forming material is actually heated. For the purpose of accuracy, the temperature distribution as an initial temperature distribution may be calculated by considering air cooling during the transfer of the press-forming material after heating in the electric furnace.

The step of analyzing press forming, which is performed by the press-forming analyzing means 13, is performed after the temperature dependency data (Young's modulus, Poisson's ratio, coefficient of thermal expansion, yield stress, stress-strain curve, specific heat, and thermal conductivity, for example), which is required by the press-forming analyzing means 13, is input to the press-forming analyzing means 13 to provide the initial temperature distribution to both the press-forming material and the tool.

In addition, in the actual warm press forming, the press-forming material may springback less after release from the tool depending on a shape of a part if held at the bottom dead point of the press and cooled for a predetermined time, whereby a better shape is obtained in some cases. Thus, in the step of analyzing press forming, the press-forming material may be held in the tool for a predetermined time for cooling. However, in the actual warm press forming, a longer cooling time lowers production efficiency. When setting the cooling time in the step of analyzing press forming, the cooling time is preferably determined in consideration of the production efficiency in the actual operation.

The necessary data of the press-forming material immediately before release from the tool and such data of the tool calculated in the step of analyzing press forming such as the shape information, the temperature distribution, the stress distribution, and the strain distribution are carried over to the next step of analyzing springback.

<Step of Analyzing Springback>

The step of analyzing springback involves a springback analysis by combining a temperature analysis and a structural analysis without consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback (Step S3).

In the step of analyzing springback in the first embodiment, the analysis is performed without consideration of the contact heat transfer between the tool and the press-forming material. Thus, in the springback analyzing step, a decrease in the temperature of the press-forming material by contact with the tool does not need to be considered. Only a decrease in temperature due to the air cooling is considered for calculation. This simplifies the calculation, and thus convergence is readily obtained compared to the analysis in consideration of the contact heat transfer.

A specific method of performing the springback analysis without consideration of the contact heat transfer between the tool and the press-forming material uses the information obtained in the step of analyzing press forming as an initial condition and performs a calculation in a state in which the stress is released at the bottom dead point while one or more nodes of the press-forming material are fixed. Stress release duration is assumed to be a predetermined time.

The necessary data such as the shape information, the temperature distribution, the stress distribution, and the strain distribution after springback is carried over to the next step of analyzing a shape.

If an assumed duration of the stress release at the bottom dead point is short, e.g., one second or shorter, only a negligible change in temperature occurs, and thus the temperature analysis does not need to be performed. In such a case, the temperature distribution in the press-forming material after the press-forming analysis is carried over as is to the next step of analyzing a shape as a temperature distribution after springback. It should be noted that the structural analysis is performed based on the temperature distribution after the press-forming analysis and the temperature dependency data, even if the temperature analysis is not performed in the step of analyzing springback.

<Step of Analyzing Shape>

A step of analyzing a shape involves an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the above-described step of analyzing springback (Step S5).

The step of analyzing a shape is performed by the shape analyzing means 17. The step of analyzing a shape involves an analysis of a change in the temperature distribution due to cooling by using data such as those of the shape information, the temperature distribution, the stress distribution, and the strain distribution after the springback analysis as an initial condition and performs the structural analysis in consideration of the thermal contraction.

In a specific method of performing the step of analyzing a shape, one or more nodes of the press-forming material are fixed such that the press-forming material is not moved during cooling. The nodes may be fixed under the same condition as in the above-described step of analyzing springback.

The temperature analysis may be performed under assumption of air cooling. However, the press-forming material in an actual operation may be assumed to be cooled on a cooling table, and the temperature analysis may be performed in consideration of contact heat transfer between the cooling table and the press-forming material to obtain a temperature analysis result that is closer to the temperature in the actual operation.

In the step of analyzing a shape, the analysis of a change in shape of the press-forming material that occurs during and after cooling, until the range of the temperature distribution in the press-forming material falls within ±5° C., is performed for the following reason.

In the actual warm press forming, in a process of decreasing the temperature of the press-forming material to an environmental temperature such as a room temperature, the change in shape of the press-forming material due to the temperature almost stops when the range of the temperature distribution of the entire press-forming material falls within ±5° C. (more preferably, within ±1° C.). Thus, also in the step of analyzing a shape, sufficient cooling time is needed to satisfy the above-described condition of the temperature distribution.

The structural analysis in the step of analyzing a shape can be performed either dynamically or statically in principle. In a dynamic analysis, time can be compressed by time scaling, and thus the calculation requires a shorter time. However, if the structural analysis is completed by the dynamic analysis, the accuracy of the calculation is reduced as a result of residual inertial force. If a more accurate calculation result is required, the entire structural analysis in the step of analyzing a shape should be performed statically. Alternatively, in order for the dynamic analysis to be advantageous, the step of analyzing a shape may be divided into two stages. The first stage may be dynamically performed and the second stage may be statically performed. If an assumed cooling time is 1001 seconds, the dynamic analysis is performed for the first 1000 seconds by compressing time, and the static analysis is performed for the remaining 1 second, for example. This reduces the calculation time and also improves the accuracy of the analysis. More preferably, a static implicit method is used for the final stage of the structural analysis in the step of analyzing a shape.

As described above, in the method of analyzing press forming in the first embodiment, the step of analyzing press forming and the step of analyzing springback are each performed by combining the temperature analysis and the structural analysis, and the step of analyzing a shape in which the change in shape due to the change in temperature is analyzed is performed by combining the temperature analysis and the structural analysis based on the shape and the temperature distribution obtained in the step of analyzing springback. Therefore, the shape after cooling in the warm press forming is estimated, allowing countermeasures for a shape defect in the warm press forming to be taken, and advantages such as reduction in the number of test steps in a design stage of a press-formed material and reduction in the cost may be obtained.

Second Embodiment

A method of analyzing press forming in a second embodiment includes performing a step of analyzing press forming by setting an initial temperature distribution for a heated press-forming material and performing a press-forming analysis by combining a temperature analysis and a structural analysis to obtain shape information, temperature distribution, stress distribution, and strain distribution after press forming, performing a step of analyzing springback by performing a springback analysis by combining a temperature analysis and a structural analysis in consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback, and performing a step of analyzing a shape by performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback.

The method of analyzing press forming in the second embodiment is same as the method of analyzing press forming in the first embodiment except that the step of analyzing springback is performed in consideration of the contact heat transfer between the tool and the press-forming material, which is not taken into consideration in the method of analyzing press forming in the first embodiment.

Therefore, a description is given below to the consideration of the contact heat transfer between the tool and the press-forming material in the step of analyzing springback in the second embodiment.

An advantage obtained by considering the contact heat transfer between the tool and the press-forming material in the step of analyzing springback is as follows.

A change in temperature resulting from release from a tool can be more correctly taken into consideration, and thus the temperature distribution in the press-forming material after springback can be more precisely calculated. As a result, the shape of the press-formed material after cooling, which is obtained in the step of analyzing a shape, can be more precisely calculated.

However, as described in the first embodiment, the convergence can be readily obtained when the contact heat transfer between the tool and the press-forming material is not taken into consideration in the step of analyzing springback. Whether the contact heat transfer is considered or not may be determined on a case-by-case basis.

In a specific analysis method that considers the contact heat transfer between the tool and the press-forming material in the step of analyzing springback, releasing of the tool is simulated by moving the tool while one or more nodes of the press-forming material are fixed such that the press-forming material is not moved. In this case, the temperature analysis is performed in consideration of heat removal due to contact with the tool and air cooling at a part that is not in contact with the tool.

The initial condition in the step of analyzing springback and carrying over of the data after springback in the first embodiment are also applicable to the second embodiment.

As described above, according to the second embodiment, the change in temperature caused by release from the tool can be more accurately taken into account, and the temperature distribution of the press-forming material after springback can be more precisely calculated. Therefore, the shape of the press-formed material after cooling, which is obtained in the step of analyzing a shape, can be more precisely calculated.

In the above-described first and second embodiments, the method of performing the analysis on the press-forming material heated to 600° C. is described under assumption of the warm press forming. However, disclosed embodiments may be used for an analysis of cold press forming if the analysis is performed in consideration of influence of heat such as processing heat and friction heat.

In addition, a method of analyzing press forming according to embodiments has great practical value for consideration of countermeasures for a shape defect when combined with the method that considers the stress distribution as disclosed in Patent Literature 1.

Third Embodiment

A method of analyzing press forming in a third embodiment is performed by an apparatus such as PC (personal computer) that runs a program. First, an overview of a configuration of the apparatus (hereinafter, referred to as the "apparatus of analyzing press forming 1") is described with reference to the block diagram in FIG. 7.

Apparatus for Analyzing Press Forming

Figure 7:
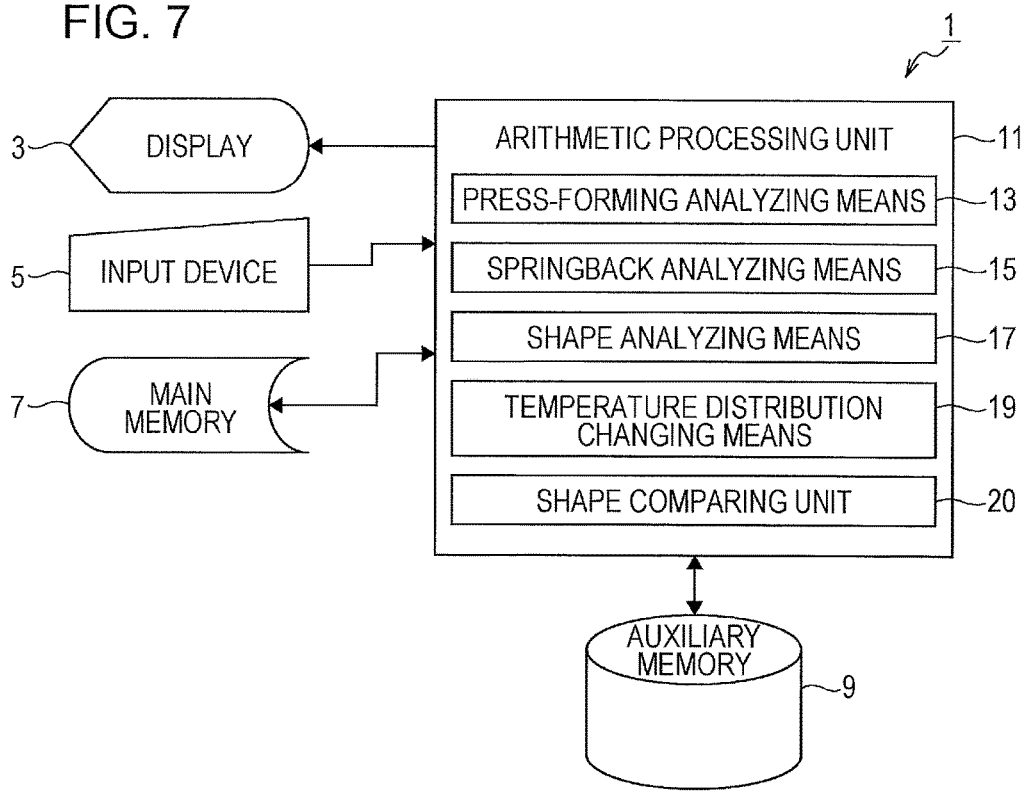
FIG. 7 is a block diagram illustrating a configuration of an apparatus according to an embodiment.

An apparatus of analyzing press forming 1 in the third embodiment is a PC (Personal Computer) and the like and includes a display 3, an input device 5, a main memory 7, an auxiliary memory 9 and an arithmetic processing unit 11, as illustrated in FIG. 7.

The display 3, the input device 5, the main memory 7, and the auxiliary memory 9 are coupled to the arithmetic processing unit 11 and each operate in response to a command from the arithmetic processing unit 11. The display 3 displays a calculation result and the like, and is an LCD monitor and the like.

The input device 5 is used by an operator for input, for example, and is a keyboard, a mouse and the like.

The main memory 7 temporarily stores data to be used in the arithmetic processing unit 11 or data being processed, for example, and is a RAM and the like. The auxiliary memory 9 stores data and the like, and is a hard disk and the like.

The arithmetic processing unit 11 is a CPU of a PC and the like, of a PC, for example. The arithmetic processing unit 11 includes a press-forming analyzing means 13, a springback analyzing means 15, a shape analyzing means 17, a temperature distribution changing means 19 and a shape comparing unit 20. The analyzers operate when the CPU and the like, runs a predetermined program. Hereinafter, the analyzers are described.

<Press-Forming Analyzing Means>

The press forming analyzing means 13 is configured to set an initial temperature distribution for a heated press-forming material and perform a press-forming analysis by combining a temperature analysis and a structural analysis to obtain shape information, temperature distribution, stress distribution, and strain distribution after press forming (before release from a tool).

<Springback Analyzing Means>

The springback analyzing means 15 is configured to perform a springback analysis by combining a temperature analysis and a structural analysis to obtain shape information, temperature distribution, stress distribution, and strain distribution after springback, based on the information obtained by the press-forming analyzing means 13.

<Shape Analyzing Means>

The shape analyzing means 17 is configured to analyze a change in shape of the press-forming material that occurs during and after cooling, until the range of the temperature distribution in the press-forming material falls within ±5° C., by combining a temperature analysis and a structural analysis based on the shape information, the temperature distribution, the stress distribution, and the strain distribution obtained by the springback analyzer 15.

The shape analyzing means 17 performs both the first step of analyzing a shape and the second step of analyzing a shape as described below.

<Temperature Distribution Changing Means>

The temperature distribution changing means 19 is configured to add a modification to the temperature distribution obtained by the springback analyzing means 15. Specifically, the temperature distribution changing means 19 adds a modification to the temperature distribution in a predetermined part of the press-forming material by a command from an operator.

<Shape Comparing Unit>

The shape comparing unit 20 is configured to compare a plurality of shapes of the press-forming materials after cooling obtained by the shape analyzing means 17. Specifically, the shape comparing unit 20 is configured to display the shapes of the press-forming materials after cooling on the display 3 so as to be visually compared by an operator.

[Method of Analyzing Press Forming]

A method of analyzing press forming in the third embodiment is performed when each of the above-described "press-forming analyzing means", "springback analyzing means", "shape analyzing means", "temperature distribution changing means", and "shape comparing unit" performs its function and includes the following steps.

Specifically, the method of analyzing press forming in the third embodiment includes performing a step of analyzing press forming including setting an initial temperature distribution for a heated press-forming material and performing a press-forming analysis by combining a temperature analysis and a structural analysis to obtain shape information, temperature distribution, stress distribution, and strain distribution in the press-forming material before release from a tool;

performing a step of analyzing springback including performing a springback analysis by combining a temperature analysis and a structural analysis without consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback;

performing a first step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback;

performing a second step of analyzing a shape including adding a modification to the temperature distribution obtained in the step of analyzing springback and performing an analysis of a change in shape of the press-forming material that occurs during and after cooling, until a range of the temperature distribution in the press-forming material falls within ±5° C., by combining a temperature analysis and a structural analysis based on the modified temperature distribution, the shape information, the stress distribution, and the strain distribution obtained in the step of analyzing springback; and performing a step of comparing shapes including comparing shapes of the press-forming materials after cooling obtained by the analysis in the second step of analyzing a shape and in the analysis the first step of analyzing a shape.

In the method of analyzing press forming in the third embodiment, the analysis is performed by combining the temperature analysis and the structural analysis in each step as described above. In the analysis performed by combining the temperature analysis and the structural analysis, the temperature distribution in the press-forming material is analyzed (temperature analysis) in consideration of air cooling and contact heat transfer between the tool and the press-forming material, for example, and a pressed condition and the like, is analyzed (structural analysis) by using temperature dependency data (Young's modulus, Poisson's ratio, thermal expansion coefficient, yield stress, stress-strain curve, specific heat, thermal conductivity and the like) corresponding to the temperature based on the obtained temperature distribution.

Figure 6:
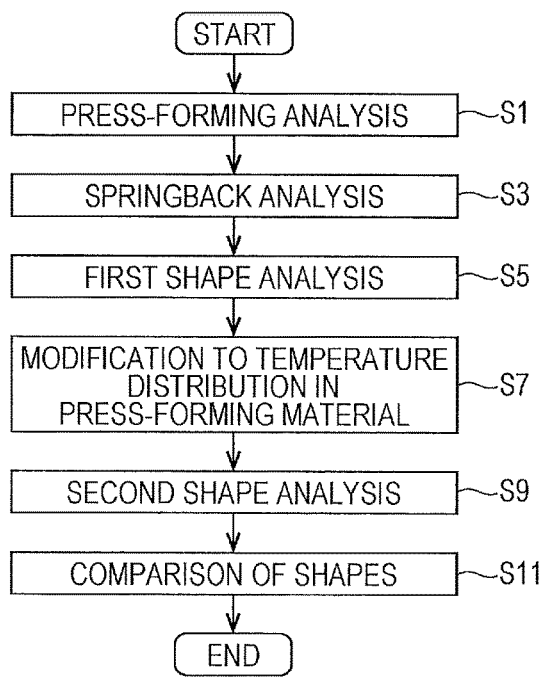
FIG. 6 is a flowchart of processing according to an embodiment.

Hereinafter, each of the above-described steps in the method of analyzing press forming in the third embodiment is described in detail with reference to the flowchart in FIG. 6. In the following description, a hat-like cross-sectional shape is obtained by a crash forming for example.

<Step of Analyzing Press Forming>

The step of analyzing press forming includes setting an initial temperature distribution for a heated press-forming material, and performing a press-forming analysis by combining a temperature analysis and a structural analysis to obtain shape information, temperature distribution, and stress distribution, and strain distribution after press forming (before release from a tool) (Step S1).

Setting of the initial temperature distribution for the heated press-forming material is described below.

In actual warm press forming, a press-forming material is sufficiently heated in an electric furnace to have a uniform temperature and then transferred to a pressing machine by a transfer robot for press forming. In the step of analyzing press forming, the initial temperature of the entire press-forming material is set to be uniform (600° C., for example) assuming that the press-forming material is actually heated. For the purpose of accuracy, the temperature distribution as an initial temperature distribution may be calculated by considering air cooling during the transfer of the press-forming material after heating in the electric furnace.

The step of analyzing press forming, which is performed by the press-forming analyzing means 13, is performed after the temperature dependency data (Young's modulus, Poisson's ratio, coefficient of thermal expansion, yield stress, stress-strain relationship, specific heat, thermal conductivity and the like), which is required by the press-forming analyzing means 13, is input to the press-forming analyzing means 13 to provide the initial temperature distribution to the press-forming material and the tool.

In addition, in the actual warm press forming, the press-forming material may spring back less after release from the tool depending on a shape of a part if held at the bottom dead point of the press and cooled for a predetermined time, whereby a better shape is obtained in some cases. Thus, in the step of analyzing press forming, the press-forming material may be held in the tool for a predetermined time for cooling. However, in the actual warm press forming, a longer cooling time lowers production efficiency. In setting of the cooling time in the step of analyzing press forming, the cooling time is preferably determined in consideration of the production efficiency in the actual operation.

The necessary data of the press-forming material immediately before release from the tool and such data of the tool calculated in the step of analyzing press forming such as the shape information, the temperature distribution, the stress distribution, and the strain distribution are carried over to the next step of analyzing springback.

<Step of Analyzing Springback>

The step of analyzing springback performs a springback analysis by combining a temperature analysis and a structural analysis without consideration of contact heat transfer between the tool and the press-forming material based on the shape information, the temperature distribution, the stress distribution, and the strain distribution obtained in the step of analyzing press forming to obtain shape information, temperature distribution, stress distribution, and strain distribution after springback (Step S3).

In the step of springback in the third embodiment, the analysis is performed without consideration of the contact heat transfer between the tool and the press-forming material. Thus, in the springback step, a decrease in the temperature of the press-forming material by contact with the tool does not need to be considered. Only a decrease in temperature due to the air cooling is considered for calculation. This simplifies the calculation. Thus, convergence is readily obtained compared to the analysis in consideration of the contact heat transfer.

A specific method of performing the springback analysis without consideration of the contact heat transfer between the tool and the press-forming material uses the information obtained in the step of analyzing press forming as an initial condition and performs a calculation in a state in which the stress is released at the bottom dead point while one or more nodes of the press-forming material are fixed. Stress release duration is assumed to be a predetermined time.

The necessary data such as the shape information, the temperature distribution, the stress distribution, and the strain distribution after springback is carried over to the next step of a first step of analyzing a shape.

If an assumed duration of the stress release at the bottom dead point is short, e.g., one second or shorter, only a negligible change in temperature occurs, and thus the temperature analysis does not need to be performed. In such a case, the temperature distribution in the press-forming material after the press-forming analysis is carried over as is to the next step of the first step of analyzing a shape as a temperature distribution after springback. It should be noted that the structural analysis is performed based on the temperature distribution after the press-forming analysis and the temperature dependency data, even if the temperature analysis is not performed in the step of analyzing springback.

Figure 8:
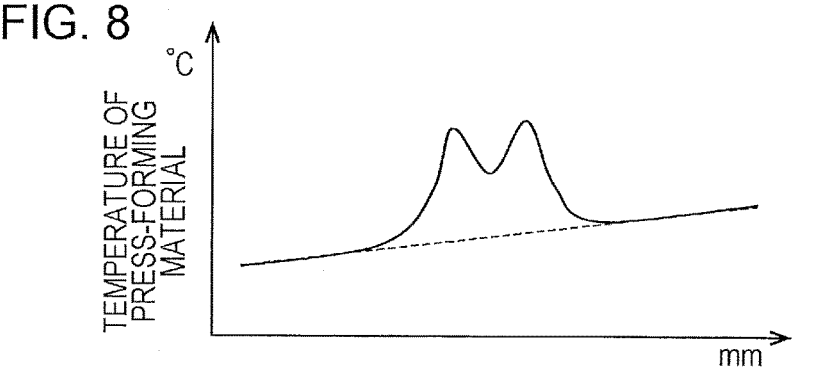
FIG. 8 is a diagram showing a temperature distribution in a cross section of a wrinkle in a hat-like cross-sectional shape according to an embodiment.

FIG. 8 is a graph showing an example of a temperature distribution of a specific part of the press-forming material obtained in the step of analyzing springback. In the graph of FIG. 8, a vertical axis represents a temperature of the press-forming material (° C.) and a horizontal axis represents a distance (mm) measured along a cross-sectional surface of the press-forming material.

When a hat-like cross-sectional shape is formed by a crash forming, under some condition of the press-forming, a flange may have a wrinkle in the process of the press forming. The temperature at the wrinkle after springback is higher than the temperature around the wrinkle. This results from that the flange is in contact with the tool during the process of the press forming and the heat of the flange is transferred to the tool, whereby the temperature of the flange decreases, but the wrinkle has a part that is not in contact with the tool, whereby the temperature of the part of the wrinkle does not decrease.

The graph of FIG. 8 indicates the temperature distribution in a part of the cross-sectional surface including the top of the wrinkle as its center and a periphery of the top including an end portion of the wrinkle. The solid line indicates the temperature distribution obtained in the step of analyzing springback. As indicated by the solid line in the graph of FIG. 8, two protrusions are seen side-by-side and a recess is seen therebetween. The recess corresponds to the top of the wrinkle. The top of the wrinkle has a low temperature, because it is in contact with the tool.

As indicated in FIG. 8, the generation of wrinkle causes the temperature distribution in the press-forming material.

<First Step of Analyzing Shape>

The first step of analyzing a shape involves an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the above-described step of analyzing springback (Step S5).

In this example, the first step of analyzing a shape is performed based on the temperature distribution including the temperature distribution in the part including the wrinkle indicated by the solid line in FIG. 8.

The first step of analyzing a shape is performed by the shape analyzer 17. The step of analyzing a shape involves an analysis of a change in the temperature distribution due to cooling by using data such as those of the shape information, the temperature distribution, the stress distribution, and the strain distribution as an initial condition and performs a structural analysis in consideration of thermal contraction.

In a specific method of performing the first step of analyzing a shape, one or more nodes of the press-forming material are fixed such that the press-forming material is not moved during cooling. The nodes may be fixed under the same condition as in the above-described step of analyzing springback.

The temperature analysis may be performed under assumption of air cooling. However, the press-forming material in an actual operation may be assumed to be cooled on a cooling table, and the temperature analysis may be performed in consideration of contact heat transfer between the cooling table and the press-forming material to obtain a result of the temperature analysis that is closer to that in the actual operation.

In the first step of analyzing a shape, the analysis of the change in shape of the press-forming material that occurs during and after cooling, until the range of the temperature distribution in the press-forming material falls within ±5° C., is performed for the following reason.

In the actual warm press forming, in a process of decreasing temperature of the press-forming material to an environmental temperature such as a room temperature, the change in shape due to the temperature almost stops when the range of the temperature distribution of the entire press-forming material falls within ±5° C. (more preferably, within ±1° C.). Thus, also in the first step of analyzing a shape, sufficient cooling time is needed to satisfy the above-described condition of the temperature distribution.

<Second Step of Analyzing Shape>

The second step of analyzing a shape involves adding a modification to the temperature distribution obtained in the step of analyzing springback and analyzing a change in shape of the press-forming material that occurs during and after cooling, until a range of the temperature distribution in the press-forming material falls within ±5° C., by combining a temperature analysis and a structural analysis based on the modified temperature distribution, the shape information, the stress distribution, and the strain distribution obtained in the step of analyzing springback (Steps S7 and S9).

The second step of analyzing a shape is same as the first step of analyzing a shape except that the shape analysis is performed after a modification is added to the temperature distribution obtained in the step of analyzing springback.

As one way of adding a modification to the temperature distribution in the press-forming material after springback, this example shows that the temperature distribution in a part including the wrinkle is modified as indicated by a dot-line in FIG. 8. In short, the temperature distribution in the part including the wrinkle is not included, i.e., the temperature distribution is the one to be obtained if no wrinkles are generated.

After the modification of the temperature distribution, a change in the temperature distribution due to cooling is analyzed based on the shape information, the stress distribution, and the strain distribution obtained in the step of analyzing springback by the shape analyzer 17, and the structural analysis in consideration of the thermal contraction is performed.

<Step of Comparing Shapes>

The step of comparing shapes compares the shapes of the press-forming materials after cooling obtained by the analysis in the first step of analyzing a shape and the analysis in the second step of analyzing a shape (Step S11).

In the step of comparing shapes, the shapes of the press-forming materials after cooling obtained by the analysis in the second step of analyzing a shape and the analysis in the first step of analyzing a shape are displayed on the display 3 so as to be compared (shapes are arranged beside one another or overlapped each other). An operator visually compares the shapes.

If there is no difference between the shapes of the press-forming materials after cooling obtained by the analysis in the first step of analyzing a shape and the analysis in the second step of analyzing a shape, it is found that the above-described modification to the temperature distribution does not affect the shape of the press-forming material after cooling. This shows that the temperature distribution before the modification does not cause a problem even if generated after springback.

Contrary to that, if there is a difference between the shapes of the press-forming materials after cooling obtained by the analysis in the first step of analyzing a shape and the analysis in the second step of analyzing a shape, it is found that the above-described modification to the temperature distribution affects the shape of the press-forming material after cooling. In such a case, if the shape after the modification to the temperature distribution is close to a target shape, the temperature distribution before the modification causes a problem if generated after springback. It is found that press forming that does not allow such a temperature distribution enables the forming material after cooling to have a shape close to the target shape. In this example, since the temperature distribution resulting from the wrinkle generation is considered to cause a problem, a press-forming method that does not generate a wrinkle is required. An example of such a method includes deep drawing in which the press-forming material is held by a blank holder while a tool is moved from the top dead point to the bottom dead point, for example, or the initial shape of the press-forming material may be changed.

As described above, the third embodiment enables us to know how the temperature distribution after springback affects the shape after cooling. Thus, countermeasures for a shape defect in the warm press forming can be taken, and advantages such as reduction in the number of test steps in a design stage of a press-formed material and reduction in the cost may be obtained.

In the above description, the temperature distribution after springback is made by adding a modification to the temperature distribution of a part (including a wrinkle) of the press-forming material. However, the modification may be added such that the entire press-forming material has a uniform temperature.

Hereinafter, a case in which the temperature distribution is modified such that the entire press-forming material has a uniform temperature is described by using the press-forming material having a hat-like cross-sectional shape as an example.

Figure 9:
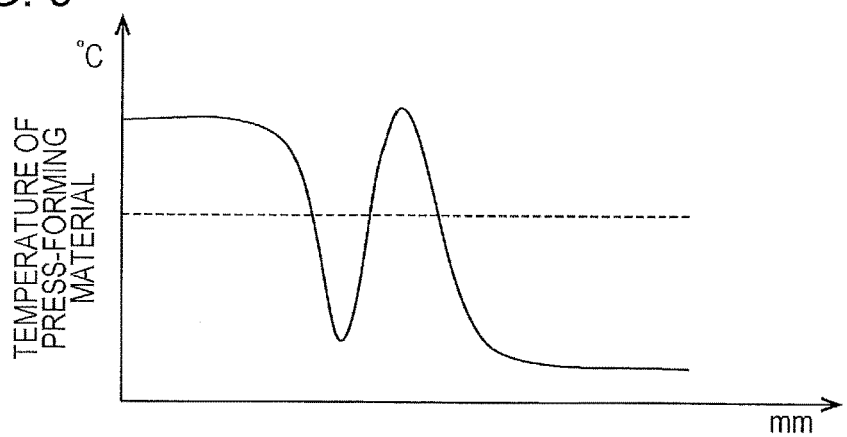
FIG. 9 is a diagram showing a half of a temperature distribution of an entire hat-like cross-sectional shape as another example according to an embodiment.

FIG. 9 is a graph showing a temperature distribution after springback in the hat-like cross-sectional shape obtained by drawing. In the graph of FIG. 9, a vertical axis represents a temperature of the press-forming material (OC) and a horizontal axis represents a distance (mm) measured from a center in the width direction along a cross-sectional surface of the press-forming material. Only a half of the hat-like cross-sectional shape in a width direction is indicated.

When the hat-like cross-sectional shape is obtained by the press forming, a top portion and a vertical portion of the hat-like cross-sectional shape are in contact with the tool for a short time, and thus the temperature thereof is less likely to decrease and remains high. However, a curved portion that extends between the top portion and the vertical portion and a flange portion are in contact with the tool for a long time, and thus the temperature thereof decreases. As a result, the temperature distribution is uneven as indicated by the solid line in the graph of FIG. 9.

If a comparison is made between the shape after cooling, which is obtained by the first step of analyzing a shape based on the uneven temperature distribution, and the result of the second step of analyzing a shape based on a uniform temperature over the entire hat-like cross-sectional shape, which is obtained by changing the uneven temperature distribution (dot-line graph in FIG. 9), it can be made clear whether the shape defect is caused by the uneven temperature distribution or by the thermal contraction occurred uniformly over the entire area.

The structural analysis in each of the first step of analyzing a shape and the second step of analyzing a shape can be performed either dynamically or statically in principle. In a dynamic analysis, time can be compressed by time scaling, and thus the calculation requires a shorter time. However, if the structural analysis is completed by the dynamic analysis, the accuracy of the calculation is reduced as a result of residual inertial force. If a more accurate calculation result is required, the entire structural analysis in the step of analyzing a shape should be performed statically. Alternatively, in order for the dynamic analysis to be advantageous, the first step of analyzing a shape and/or the second step of analyzing a shape may be divided into two stages. The first stage may be dynamically performed and the second stage may be statically performed. If an assumed cooling time is 1001 seconds, the dynamic analysis is performed for the first 1000 seconds by compressing the time, and the static analysis is performed for the remaining 1 second, for example. This reduces the calculation time and also improves the accuracy of the analysis. More preferably, a static implicit method is used for the final stage of the structural analysis in the first step of analyzing a shape and the second step of analyzing a shape.

Fourth Embodiment

A method of analyzing press forming in a fourth embodiment includes: performing a step of analyzing press forming including setting an initial temperature distribution for a heated press-forming material and performing a press-forming analysis by combining a temperature analysis and a structural analysis to obtain shape information, temperature distribution, stress distribution, and strain distribution before release from a tool;

performing a step of analyzing springback including performing a springback analysis by combining a temperature analysis and a structural analysis in consideration of contact heat transfer between the tool and the press-forming material based on the shape information, the temperature distribution, the stress distribution, and the strain distribution obtained in the step of analyzing press forming to obtain shape information, a temperature distribution, stress distribution, and strain distribution after springback;

performing a first step of analyzing a shape including performing an analysis of a change in shape of the press-forming material that occurs during and after cooling, until a range of the temperature distribution in the press-forming material falls within ±5° C., by combining a temperature analysis and a structural analysis based on the shape information, the temperature distribution, the stress distribution, and the strain distribution obtained in the step of analyzing springback;

performing a second step of analyzing a shape including adding a modification to the temperature distribution obtained in the step of analyzing springback and performing an analysis of a change in shape of the press-forming material that occurs during and after cooling, until a range of the temperature distribution in the press-forming material falls within ±5° C., by combining a temperature analysis and a structural analysis based on the modified temperature distribution, the shape information, the stress distribution, and the strain distribution obtained in the step of analyzing springback; and performing a step of comparing shapes including comparing shapes of the press-forming materials after cooling obtained in the second step of analyzing a shape and the first step of analyzing a shape.

The method of analyzing press forming of the fourth embodiment is same as the method of analyzing press forming in the third embodiment except that the step of analyzing springback is performed in consideration of the contact heat transfer between the tool and the press-forming material, which is not taken into consideration in the method of analyzing press forming in the third embodiment.

Therefore, a description is given below to the consideration of contact heat transfer between the tool and the press-forming material in the step of analyzing springback in this embodiment.

An advantage obtained by considering the contact heat transfer between the tool and the press-forming material in the step of analyzing springback is as follows.

A change in temperature caused by release from the tool can be more accurately taken into account, and the temperature distribution in the press-forming material after springback can be more precisely calculated. As a result, the shape of the press-formed material after cooling can be more precisely calculated in the step of analyzing a shape.

However, as described in the third embodiment, the convergence can be readily obtained when the contact heat transfer between the tool and the press-forming material is not taken into consideration in the step of analyzing springback. Whether the contact heat transfer is considered or not may be determined on a case-by-case basis.

In a specific analysis method that considers the contact heat transfer between the tool and the press-forming material in the step of analyzing springback, releasing of the tool is simulated by moving the tool while one or more nodes of the press-forming material are fixed such that the press-forming material is not moved. In this case, the temperature analysis is performed in consideration of heat removal due to contact with the tool and air cooling at a part that is not in contact with the tool.

The initial condition in the step of analyzing springback and carrying over of the data after springback in the third embodiment are also applicable to the fourth embodiment.

As described above, according to the fourth embodiment, the change in temperature caused by release from the tool can be more accurately taken into account, and the temperature distribution in the press-forming material after springback can be more precisely calculated. Therefore, the shape of the press-formed material after cooling, which is obtained in the step of analyzing a shape, can be more precisely calculated.

In the above-described third and fourth embodiments, the method of performing the analysis on the press-forming material heated to 600° C. is described under assumption of the warm press forming. However, disclosed embodiments may be used for an analysis of cold press forming if the analysis is performed in consideration of influence of heat such as processing heat and friction heat.

In addition, a method of analyzing press forming according to embodiments has great practical value for consideration of countermeasures for a shape defect when combined with the method that considers the stress distribution as disclosed in Patent Literature 1.

EXAMPLES

Example 1

An experiment that was performed to ensure advantages obtained in the first and second embodiments is described below.

Figure 3:
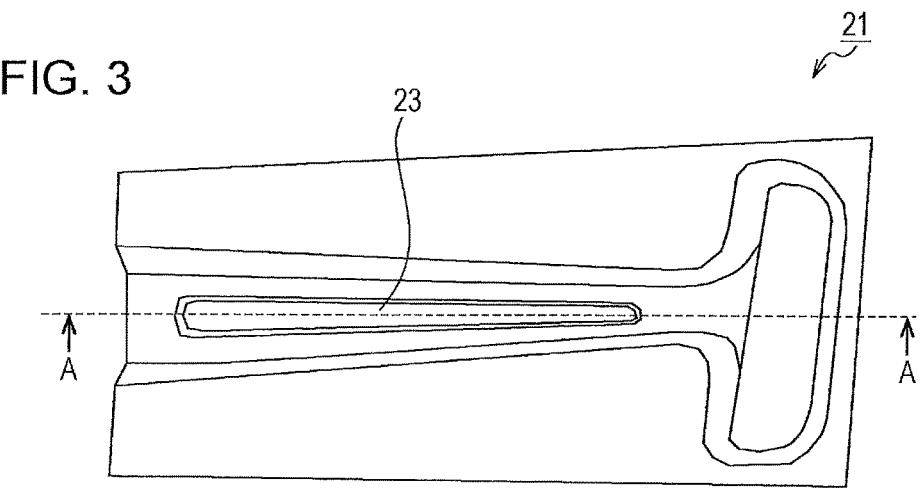
FIG. 3 is a schematic view showing an actual press-formed material in an example according to an embodiment.

In the experiment, an upper part 21 of a B-pillar which is illustrated in FIG. 3 (pillar in an area between front seats and rear seats) of a car was actually formed by the warm press forming and a simulation analysis was performed for the upper part 21 by using the method of analyzing press forming according to embodiments. A comparison was made to the upper part 21 was actually formed and a result of the simulation analysis.

First, the actual warm press forming is briefly described. A high strength steel sheet of 980 MPa was used as a press-forming material and an initial shape thereof was a parallelogram having a base of 650 mm, a height of 300 mm, and a thickness of 1.4 mm. The press-forming material was heated to 680° C. in an electric furnace, and then placed in the tool of a pressing machine by a transfer robot for press forming. A temperature at the start of the press forming was 600° C. (changes in temperature under such a condition were measured in advance by a thermocouple mounted on the center of the press-forming material, and the temperature of the material at the completion of the attachment to the pressing machine was 600° C.). In the press forming, drawing was performed under a blank holder pressure of 45 tonf. An average speed of the press forming was 100 mm/s. The tool was released immediately after reaching the bottom dead point and the press-forming material was cooled to a room temperature to obtain a press-formed material (hereinafter, referred to as an "actual press-formed material"). Finally, a shape of a surface of the actual press-formed material was measured using a non-contact three-dimensional shape measuring device.

Next, the simulation analysis that was performed by using the method of analyzing press forming according to embodiments is described.

As in the method of analyzing press forming according to embodiments, the simulation analysis sequentially performed the step of analyzing press forming, the step of analyzing springback, and the step of analyzing a shape.

Hereinafter, an input condition and an analysis condition, for example, in each of the analyzing steps are described.

<Step of Analyzing Press Forming>

First, necessary data and conditions were input into the press-forming analyzing means 13 to perform the press-forming analysis by the press-forming analyzing means 13. Hereinafter, the data and the conditions that were input are briefly described.

The property data of each material was data measured before this experiment by using the material having the same steel grade as the press-forming material used in the above-described actual warm press forming. Specifically, the temperature dependency data of a heat flux, thermal conductivity, thermal expansion coefficient, Young's modulus, and Poisson's ratio was measured, and a tensile test was conducted at 400° C., 500° C., and 600° C. to obtain a stress-strain diagram model.

An initial shape of the press-forming material used in the above-described actual warm press forming was modeled as a shell element at its center in the thickness direction. The tool used in the above-described actual warm press forming was modeled as a shell element at its surface. Furthermore, the press-forming material was assumed as a deformable body, and the tool was assumed as a rigid body.

In the press-forming analysis, when a distance between the surface of the press-forming material and the surface of the tool is less than 0.01 mm, the press-forming material and the tool were considered to be in contact with each other, and a heat flux was calculated from the contact heat transfer. Furthermore, when the distance is 0.01 mm or more, the press-forming material was considered to be cooled by air, and radiation and convection current was taken into consideration. The emissivity of the press-forming material was set at 0.75.

In addition, the initial temperature of the press-forming material was assumed to be a constant temperature of 600° C.

<Step of Analyzing Springback>

Next, the springback analysis was performed by the springback analyzing means 15. In the springback analysis, movements at two nodes on the punch bottom and at one node on the flange were fixed, and the stress was released while the tool was positioned at the bottom dead point. The stress release duration was set at 0.5 seconds, and the temperature analysis was also performed on the assumption that the press-forming material was cooled by the air during this period.

<Step of Analyzing Shape>

Next, the analysis of a change in shape due to cooling was performed by the shape analyzing means 17. In the shape analysis, cooling by air was assumed to be performed for 1000 seconds and a dynamic explicit method was used for a structural analysis for this period in view of inertial force, and then a static implicit method was used for the structural analysis for one second so as to eliminate influence of lowered accuracy caused due to the inertial force. The range of the temperature distribution in the material at the completion of the shape analysis was within ±1° C.

Hereinafter, a method of comparing an actual press-formed material shape and the shape obtained as the simulation analysis result is described.

As described above, the measured shape of the surface of the actual press-formed material and the shape obtained by the above-described simulation analysis were obtained at different positions of the press-forming material. Thus, to enable comparison, the shapes are processed such that each shape becomes a surface in contact with a surface of the tool. The process was performed as described below. Since the measured shape of the surface of the actual press-formed material was a shape viewed from the above, the measured shape was displaced downwardly by 1.4 mm, which is same as the thickness of the press-forming material, to obtain the actual press-formed material shape.

In addition, since the press-forming material used in the simulation analysis was modeled at its center in the thickness direction, the shapes obtained in the above-described simulation analysis were each displaced downwardly by 0.7 mm, which is a half of the thickness.

In the following description, a shape based on the shape of the actual press-formed material is referred to as an actual press-formed material shape, a shape based on the shape obtained after the springback analysis is referred to as a shape after the springback analysis, and a shape based on the shape obtained after the shape analysis is referred to as a shape after the shape analysis. In addition to these shapes, a shape of a surface of the tool, which is used for comparison, is referred to as a tool surface shape. The tool used in the above-described simulation analysis was used to obtain the tool surface shape.

These four shapes (the actual press-formed material shape, the shape after the springback analysis, the shape after the shape analysis, and the tool surface shape) were compared in the A-A arrow cross-section in FIG. 3 after the positions of the four shapes were adjusted by using a shape comparison software such that outlines of beads 23 of the punch bottoms in FIG. 3 are closely fitted to each other.

Figure 4:
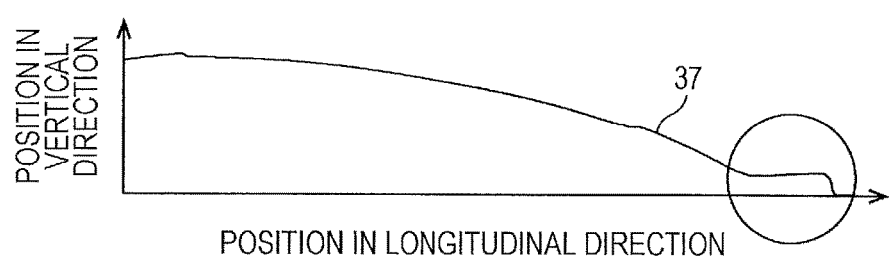
FIG. 4 is a diagram showing a cross-sectional shape of a tool used in an example according to an embodiment.
Figure 5:
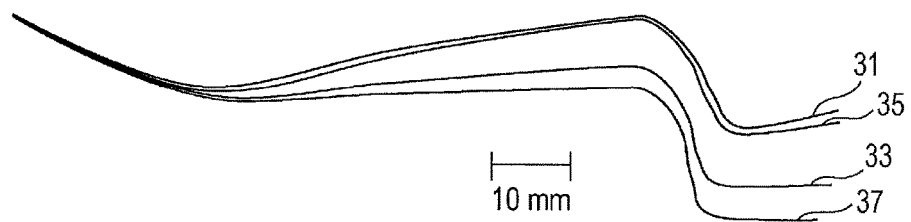
FIG. 5 is a diagram for comparing shapes of a tool, an actual press-formed material, and an analysis result according to an embodiment.

In FIG. 4, a cross-sectional shape of the tool surface shape 37 is shown as an example of the A-A arrow cross-section. As a result of the comparison of the four shapes, a significant shape defect is seen at a portion indicated by a circle in FIG. 4. FIG. 5 shows portions of the four shapes each corresponding to the portion indicated by the circle in a magnified and superimposed state. In FIG. 5, the reference numerals 31, 37, 33, 35 indicate the actual press-formed material shape, the tool surface shape, the shape after the springback, and the shape after the shape analysis, respectively.

As seen from FIG. 5, the shape after the springback analysis 33 and the actual press-formed material shape 31 are largely different from each other. However, the shape after the shape analysis 35 is substantially the same as the actual press-formed material shape 31. This result shows that the shape analysis performed in addition to the springback analysis improves the accuracy of the analysis for the warm press forming in which the temperature largely decreases after release from the tool.

Example 2

An experiment that was performed to ensure advantages obtained in the third and fourth embodiments is described below.

Figure 10:
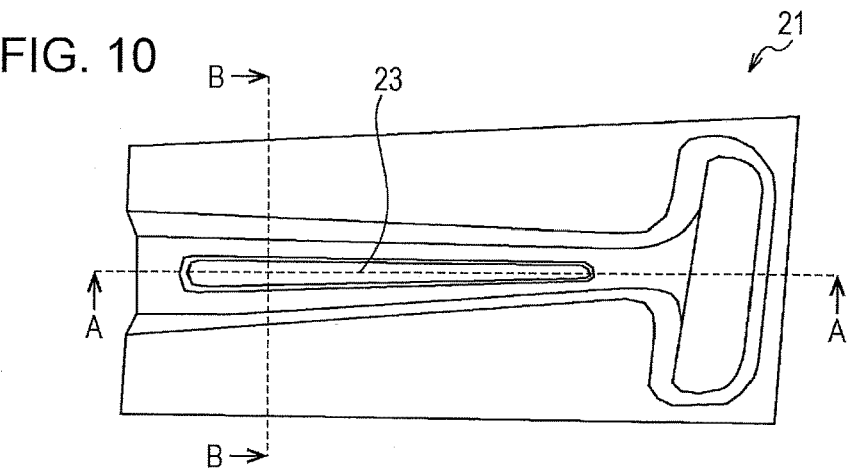
FIG. 10 is a schematic view showing an actual press-formed material according to an embodiment.

As in the first example, in the experiment, an upper part 21 of a B-pillar which is illustrated in FIG. 10 (pillar in an area between front seats and rear seats) of a car was actually formed by the warm press forming and a simulation analysis was performed for the upper part 21 by using the method of analyzing press forming according to embodiments. A comparison was made to the upper part 21 actually formed and a result of the simulation analysis.

First, the actual warm press forming is briefly described. A high strength steel sheet of 980 MPa was used as a press-forming material and an initial shape thereof was a parallelogram having a base of 650 mm, a height of 300 mm, and a thickness of 1.4 mm. The press-forming material was heated in an electric furnace to 680° C., and then placed in the tool of a pressing machine by a transfer robot for press forming. A temperature at the start of press forming was 600° C. (changes in temperature under such a condition was measured in advance by a thermocouple attached on the center of the press-forming material, and the temperature of the material at the completion of the attachment to the pressing machine was 600° C.). In the press forming, drawing was performed under a blank holder pressure of 45 tonf. An average speed of the press forming was 100 mm/s. The tool was released immediately after reaching the bottom dead point and the press-forming material was cooled to a room temperature to obtain a press-formed material (hereinafter, referred to as an "actual press-formed material"). Finally, a shape of a surface of the actual press-formed material was measured using a non-contact three-dimensional shape measuring device.

Next, the simulation analysis that was performed by using the method of analyzing press forming according to embodiments is described.

As in the method of analyzing press forming according to embodiments, the simulation analysis sequentially performed the step of analyzing press forming, the step of analyzing springback, the first step of analyzing a shape, and the second step of analyzing a shape.

Hereinafter, an input condition and an analysis condition, for example, in each of the analyzing steps are described.

<Step of Analyzing Press Forming>

First, necessary data and conditions were input into the press-forming analyzing means 13 to perform the press-forming analysis by the press-forming analyzing means 13. Hereinafter, the data and the conditions that were input are briefly described.

The property data of each material was data measured before this experiment by using the material having the same steel grade as the press-forming material used in the above-described actual warm press forming. Specifically, the temperature dependency data of a specific heat, thermal conductivity, thermal expansion coefficient, Young's modulus, and Poisson's ratio was measured, and a tensile test was conducted at 400° C., 500° C., and 600° C. to obtain a stress-strain diagram model.

An initial shape of the press-forming material used in the above-described actual warm press forming was modeled as a shell element at its center in the thickness direction. The tool used in the above-described actual warm press forming was modeled as a shell element at its surface. Furthermore, the press-forming material was assumed as a deformable body, and the tool was assumed as a rigid body.

In the press-forming analysis, when a distance between the surface of the press-forming material and the surface of the tool is less than 0.01 mm, the press-forming material and the tool were considered to be in contact with each other, and a heat flux was calculated from the contact heat transfer. Furthermore, when the distance is 0.01 mm or more, the press-forming material was considered to be cooled by air, and radiation and convection current was taken into consideration. The emissivity of the press-forming material was set at 0.75.

In addition, the initial temperature of the press-forming material was assumed to be a constant temperature of 600° C.

<Step of Analyzing Springback>

Next, the springback analysis was performed by the springback analyzing means 15. In the springback analysis, movements at two nodes on the punch bottom and at one node on the flange were fixed, and the stress was released while the tool was positioned at the bottom dead point. The stress release duration was set at 0.5 seconds, and the temperature analysis was also performed on the assumption that the press-forming material was cooled by the air during this period.

Figure 11:
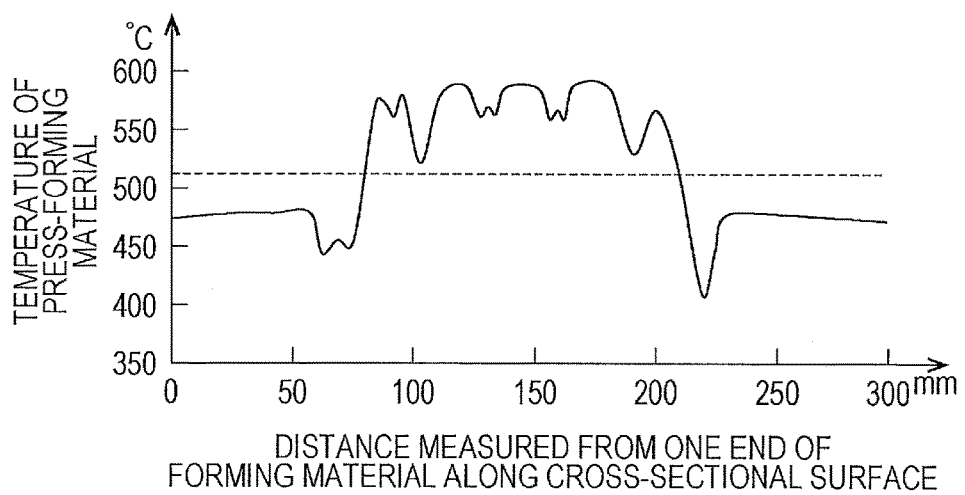
FIG. 11 is a diagram showing a temperature distribution of the actual press-formed material according to an embodiment.

FIG. 11 is a graph showing a temperature distribution in the press-forming material after the springback analysis in a B-B arrow cross-section in FIG. 10. In FIG. 11, a vertical axis represents a temperature of the press-forming material (° C.) and a horizontal axis represents a distance (mm) measured from an end of the press-forming material along a cross-sectional surface. As indicated by the solid graph, the press-forming material after the springback analysis has an uneven temperature distribution. Such an uneven temperature distribution is resulted from the difference of time in contact with the tool in the process of press forming.

<First Step of Analyzing Shape>

Next, the analysis of a change in shape due to cooling was performed by the shape analyzing means 17 based on the temperature distribution, the shape information, and the stress distribution, and the strain distribution after springback. In the shape analysis, cooling by air was assumed to be performed for 1000 seconds and a dynamic explicit method was used for a structural analysis for this period in view of internal force, and then a static implicit method was used for the structural analysis for one second so as to eliminate influence of lowered accuracy due to the inertial force. The range of the temperature distribution in the material at the completion of the shape analysis was within ±1° C.

Here, the shape after cooling that was obtained by the first step of analyzing a shape is described in comparison with an actual press-formed material shape.

As described above, the measured shape of the surface of the actual press-formed material and the shape obtained by the above-described simulation analysis were obtained at different positions of the press-forming material. Thus, to enable comparison, the shapes are processed such that each shape becomes a surface in contact with a surface of the tool. The process was performed as described below. Since the measured shape of the surface of the actual press-formed material was a shape viewed from the above, the measured shape was displaced downwardly by 1.4 mm, which is the same as thickness of the press-forming material, to obtain the actual press-formed material shape.

In addition, since the press-forming material used in the simulation analysis was modeled at its center in the thickness direction, the shapes obtained in the above-described simulation analysis were each displaced downwardly by 0.7 mm, which is a half of the thickness.

In the following description, a shape based on the shape of the actual press-formed material is referred to as an actual press-formed material shape, a shape based on the shape obtained after the springback analysis is referred to as a shape after the springback analysis, and a shape based on the shape obtained after the first shape-analysis is referred to as a shape after the first shape-analysis. In addition to these shapes, a shape of a surface of the tool, which is used for comparison, is referred to as a tool surface shape. The tool used in the above-described simulation analysis was used to obtain the tool surface shape.

These four shapes (the actual press-formed material shape, the shape after the springback analysis, the shape after the first shape-analysis, and the tool surface shape) were compared in the A-A arrow cross-sections in FIG. 10 after the positions of the four shapes are adjusted by a shape comparison software such that outlines of beads 25 of the punch bottom in FIG. 10 are closely fitted with each other.

Figure 12:
FIG. 12 is a diagram showing a cross-sectional shape of a tool used in an example according to an embodiment.
Figure 13:
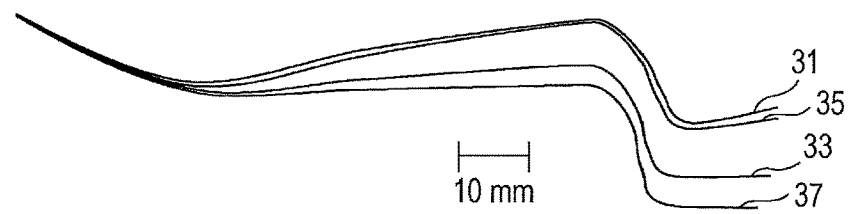
FIG. 13 is a diagram indicating shapes obtained in a first step of analyzing a shape in an according to an embodiment.

In FIG. 12, a cross-sectional shape of the tool surface shape 37 is shown as an example of the A-A arrow cross-section. As a result of the comparison of the four shapes, a significant shape defect is seen at a portion indicated by a circle in FIG. 12. FIG. 13 shows portions of the four shapes each corresponding to the portion indicated by the circle in a magnified and superimposed state. In FIG. 13, the reference numerals 31, 37, 33, 35 indicate the actual press-formed material shape, the tool surface shape, the shape after the springback analysis, and the shape after the first shape analysis, respectively.

As seen from FIG. 13, the shape after the springback analysis 33 and the actual press-formed material shape 31 are largely different from each other. However, the shape after the first shape-analysis 35 is substantially the same as the actual press-formed material shape 31. This result shows that the first shape-analysis performed in addition to the springback analysis improves the accuracy of the analysis for the warm press forming in which the temperature largely decreases after release from the tool.

<Second Step of Analyzing Shape>

Next, a modification was added to the uneven temperature distribution in the press-forming material after the analysis such that the temperature distribution in the entire press-forming material has a uniform temperature of 510° C. The temperature distribution after the modification is indicated by a dot-line graph in FIG. 11.

A shape analysis was performed to analyze a change in shape due to cooling based on the modified temperature distribution after springback, the shape information, the stress distribution, and the strain distribution after springback, and the shape of the press-forming material after cooling was calculated. The analysis conditions in the second step of analyzing a shape are same as those in the first step of analyzing shape except for the temperature distribution.

<Step of Comparing Shapes>

Next, a comparison was made between the shape after the first shape-analysis 35, which was obtained in the first step of analyzing a shape, and the shape after the second shape-analysis 39 (see FIG. 14), which was obtained in the second step of analyzing a shape, by the shape comparing unit 20.

Figure 14:
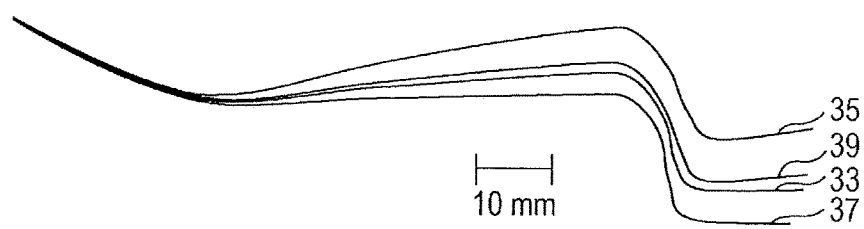
FIG. 14 is a diagram used for explanation of a step of comparing shapes.

FIG. 14 shows portions of the shape after the first shape-analysis 35 and the shape after the second shape-analysis 39 each corresponding to the portion indicated by the circle in FIG. 12. In FIG. 14, the shape after springback analysis 33 and the tool surface shape 37 are also indicated for comparison.

As illustrated in FIG. 14, the shape after the first shape-analysis 35 is largely different from the tool surface shape 37. However, the shape after the second shape-analysis 39 is close to the tool surface shape 37 and also close to the shape after the springback analysis 33. This result shows that the temperature distribution after springback that was modified to be even reduces change in shape, which may be caused by subsequent cooling.

This indicates that the shape defect occurring during cooling is prevented by making the temperature distribution after springback close to be even. The temperature distribution after springback may be made close to be even by making an average press-forming speed faster, for example. The speeding-up of the average press-forming speed shortens contact time between the press-forming material and the tool, thereby preventing decrease in temperature at a part of the press-forming material in contact with the tool. As a result, the temperature distribution in the press-forming material is made to be even.

In this example, the warm press forming was actually performed at the average press-forming speed of 150 mm/s, which is 1.5 times the press-forming speed in the above example. The other conditions were same as those in the above example. As a result, the advantage of reduction in shape defect was obtained.

REFERENCE SIGNS LIST

1 Apparatus for analyzing press forming
3 Display
5 Input device
7 Main memory
9 Auxiliary memory
11 Arithmetic processing unit
13 Press-Forming analyzing means
15 Springback analyzing means
17 Shape analyzing means
19 Temperature distribution changing means
20 Shape comparing unit
21 Upper part of B-pillar
23 Bead
31 Actual press-formed material shape
33 Shape after springback analysis
35 Shape after the shape analysis (shape after the first shape-analysis)
37 Tool surface shape
39 Shape after second shape-analysis

The invention claimed is:

1. A method of warm press-forming on a high strength steel sheet, the method comprising:
   transferring a shape of a tool to a press-forming material by pressing the tool to the press-forming material; and
   at the time of transferring, estimating the shape after cooling in warm press-forming and analyzing countermeasures for a shape defect after warm press-forming using a computer, and taking the countermeasures, the estimating and analyzing comprising:
      analyzing press-forming of a heated press-forming material before the press-forming material is released from a press-forming tool, the analyzing press-forming including (i) setting an initial temperature distribution for the heated press-forming material and (ii) performing a press-forming analysis by combining temperature analysis and structural analysis to obtain shape information, temperature distribution, stress distribution, and strain distribution;
      analyzing springback without consideration of contact heat transfer between the press-forming tool and the press-forming material by combining temperature analysis and structural analysis based on the shape information, the temperature distribution, the stress distribution, and the strain distribution obtained in analyzing the press forming;
      analyzing a first change in cooling shape of the press-forming material that occurs during and after cooling by combining temperature analysis and structural analysis based on the at least one of the shape information, the temperature distribution, the stress distribution, and the strain distribution obtained in the analyzing springback;
      modifying the temperature distribution obtained in the analyzing springback and then re-analyzing a second change in cooling shape of the press-forming material that occurs during and after cooling by combining temperature analysis and structural analysis based on the modified temperature distribution and the shape information, the stress distribution, and the strain distribution obtained in the analyzing springback; and
      comparing shapes of the press-forming materials obtained by the analyzing the first change and the re-analyzing the second change in cooling shape, the comparing being performed after cooling,
   wherein the analyzing the first change and the re-analyzing the second change in cooling shape is performed until a temperature distribution in the press-forming material is within the range of ±5° C.

2. A method of warm press-forming on a high strength steel sheet, the method comprising:
   transferring a shape of a tool to a press-forming material by pressing the tool to the press-forming material; and
   at the time of transferring, estimating the shape after cooling in warm press-forming and analyzing countermeasures for a shape defect after warm press-forming using a computer, and taking the countermeasures, the estimating and analyzing comprising:
      analyzing press-forming of a heated press-forming material before the press-forming material is released from a press-forming tool, the analyzing press-forming including (i) setting an initial temperature distribution for the heated press-forming material and (ii) performing a press-forming analysis by combining temperature analysis and structural analysis to obtain shape information, temperature distribution, stress distribution, and strain distribution;

analyzing springback in consideration of contact heat transfer between the press-forming tool and the press-forming material by combining temperature analysis and structural analysis based on the shape information, the temperature distribution, the stress distribution, and the strain distribution obtained in analyzing the press forming;

analyzing a first change in cooling shape of the press-forming material that occurs during and after cooling by combining temperature analysis and structural analysis based on the at least one of the shape information, the temperature distribution, the stress distribution, and the strain distribution obtained in the analyzing springback;

modifying the temperature distribution obtained in the analyzing springback and then re-analyzing a second change in cooling shape of the press-forming material that occurs during and after cooling by combining temperature analysis and structural analysis based on the modified temperature distribution and the shape information, the stress distribution, and the strain distribution obtained in the analyzing springback; and comparing shapes of the press-forming materials obtained by the analyzing the first change and the re-analyzing the second change in cooling shape, the comparing being performed after cooling, wherein the analyzing the first change and the re-analyzing the second change in cooling shape is performed until a temperature distribution in the press-forming material is within the range of ±5° C.

3. The method of warm press-forming on a high strength steel sheet according to claim 1, wherein the structural analysis in the analyzing the first change and re-analyzing the second change in shape includes performing a static implicit method as a final step.

4. The method of warm press-forming on a high strength steel sheet according to claim 2, wherein the structural analysis in the analyzing the first change and re-analyzing the second change in shape includes performing a static implicit method as a final step.

5. The method of warm press-forming on a high strength steel sheet according to claim 1, wherein the re-analyzing the second change in cooling shape includes modifying the temperature distribution of the entire press-forming material obtained in the analyzing springback to be uniform at the time of re-analyzing the second change in cooling shape.

6. The method of warm press-forming on a high strength steel sheet according to claim 2, wherein the re-analyzing the second change in cooling shape includes modifying the temperature distribution of the entire press-forming material obtained in the analyzing springback to be uniform at the time of re-analyzing the second change in cooling shape.

* * * * *